United States Patent [19]

Ito et al.

[11] 4,364,992

[45] Dec. 21, 1982

[54] TWO LAYER ABSORBENT ARTICLE WITH SUPER WATER-ABSORBING POLYMER

[75] Inventors: Osamu Ito, Utsunomiya; Kazunori Nishizawa, Funabashi, both of Japan

[73] Assignee: Kao Soap Co., Ltd., Tokyo, Japan

[21] Appl. No.: 273,156

[22] Filed: Jun. 12, 1981

[30] Foreign Application Priority Data

Jun. 23, 1980 [JP] Japan ................................. 55/84995

[51] Int. Cl.³ ............................................... B32B 5/16
[52] U.S. Cl. .................................. 428/283; 128/284; 128/287; 428/288; 428/398
[58] Field of Search ................ 128/287, 284; 428/281, 428/282, 283, 284, 288, 398

[56] References Cited

U.S. PATENT DOCUMENTS

| | | | |
|---|---|---|---|
| 3,670,731 | 6/1972 | Harmon | 128/284 |
| 3,901,236 | 8/1975 | Assarsson et al. | 128/284 |
| 4,041,951 | 8/1977 | Sanford | 128/287 |
| 4,093,776 | 6/1978 | Aoki et al. | 428/402 |

Primary Examiner—Marion McCamish
Attorney, Agent, or Firm—Flynn, Thiel, Boutell & Tanis

[57] ABSTRACT

An absorbent article comprising an upper, first, absorbing layer formed so that its density under a load of 35 g/cm² is lower than 0.045 g/cm³ both in the dry state and in the wet state and the weight per square meter is 15 to 50 g, and a lower, second, absorbing layer having a super water-absorbing polymer fixed thereto.

7 Claims, 10 Drawing Figures

TWO LAYER ABSORBENT ARTICLE WITH SUPER WATER-ABSORBING POLYMER

The present invention relates to an absorbent article.

Various disposable absorbent articles, such as diapers and sanitary napkins, have been proposed. For example, there are known (1) a diaper comprising a tissue paper sheet, a fluff pulp layer, a tissue paper sheet and a liquid-permeable top sheet, which are piled in that order on a liquid-impermeable sheet, (2) a diaper in which a super water-absorbing polymer is used instead of the fluff pulp, and (3) a sanitary napkin comprising a tissue paper sheet, a super water-absorbing polymer fixed layer, a fluff pulp layer, a rayon fiber layer and a liquid-permeable top sheet, which are piled in that order on a liquid-impermeable sheet. In some sanitary napkins, the pile order is different from the above-stated order.

The present invention relates to an absorbent article as mentioned above, and more particularly, the present invention relates to an improvement in such absorbent articles in which a super water-absorbing polymer is used as the absorbent, instead of a fluff pulp. The idea of using a super water-absorbing polymer instead of a fluff pulp has been known and trial products have been marketed. However, each of these products is defective in one point or another and they are not accepted by consumers. In order for these absorbent articles to be accepted by consumers, the following requirements should be satisfied. More specifically, the absorbent article should rapidly receive and absorb fluid discharged from the body and should retain the discharged fluid without wetting the skin with the discharged fluid, i.e., the so-called wet back amount should be reduced. Furthermore, because the absorbent article is thrown away after it is used, the cost thereof should be low. In order to reduce the cost, the structure of the absorbent article should be simplified as much as possible and the manufacturing efficiency should be increased. These requirements will now be further described with reference to a disposable diaper, although the same reasoning holds good also with respect to a sanitary napkin or the like. In the case of a known disposable diaper, especially when a fluff pulp is used, in order to satisfy the above-stated requirements, especially to increase the absorbing speed, the liquid-permeable top sheet should be rendered hydrophilic as much as possible and the density of the fluff pulp should be reduced, for example, to 0.08 to 0.1 g/cm$^3$. Furthermore, it is known that in order to render the surface of the fluff pulp hydrophilic, a treatment with a minute amount of a surface active agent is avoided or the amount of an oil component exuding from the resin is reduced. Furthermore, as a means for reducing the wet back amount, there has been adopted a method in which a porous liquid-permeable sheet is rendered as hydrophobic as possible, a certain thickness is given to this sheet or a certain arrangement is made so that the fluid diffusion rate in the fluff pulp is increased. In the case of a standard size product, the fluff pulp is used in an amount of 35 to 40 g per sheet. The manufacturing cost of the absorbent article is therefore influenced by the market price of pulp, which readily changes. Furthermore, for the disposable type of absorbent article, large quantities of pulps are discarded and problems of conserving resources arise. Incidentally, about 300,000,000 diapers were thrown away in Japan in the year 1979. Assuming that a fluff pulp is used in an amount of 30 g/sheet on the average, about 9,000 tons of pulp were discarded. In view of these background considerations, there have recently been proposed disposable diapers in which a layer of a powder of a super water-absorbing polymer is fixed, for example (1) by sandwiching the polymer layer between two papers, (2) by mixing the polymer with a fluff pulp and compressing the mixture, (3) by using a non-woven fabric as a support for the polymer or (4) by merely mixing such super water-absorbing polymer with a fluff pulp, in order to reduce the amount used of the fluff pulp. Furthermore, there is known a product obtained by sandwiching a powder of a super water-absorbing polymer between two papers, piling a porous liquid-permeable sheet on the assembly and integrating the pile with a liquid-impermeable back sheet. These known absorbent articles, however, are still insufficient, especially with respect to the absorbing speed, among the above-stated requirements, namely, a long time is required for the absorption. Moreover, when these absorbent articles are actually used, the fluid is not completely absorbed and the absorbent articles leak fluid.

We made researches with a veiw to eliminating the foregoing defects involved in the conventional absorbent articles, and we have now completed the present invention.

More specifically, in accordance with the present invention, there is provided an absorbent article comprising a first absorbing layer forming an upper layer and a second absorbing layer forming a lower layer, wherein the first absorbing layer is formed so that the density thereof under a load of 35 g/cm$^2$ is lower than 0.045 g/cm$^3$ both in the dry state and in the wet state and the weight per square meter is 15 to 50 g, and a super water-absorbing polymer is fixed to the second absorbing layer.

In the instant specification, by the term "the upper and lower layers", it is meant that the first absorbing layer is located at a position higher (closer to the fluid-receiving portion) than the second absorbing layer. Incidentally, the density in the wet state does not include the density of absorbed water.

The absorbent article of the present invention is characterized by the features that (1) fluid is promptly absorbed, (2) the rate of diffusion of fluid in the absorbent is very high, (3) the weight of the absorbent as a whole is small and a certain thickness is imparted to the absorbent, (4) the wet back amount is very small and (5) the absorbent article can be manufactured very simply.

The present invention will now be described in detail with reference to the accompanying drawings.

Figure 1:
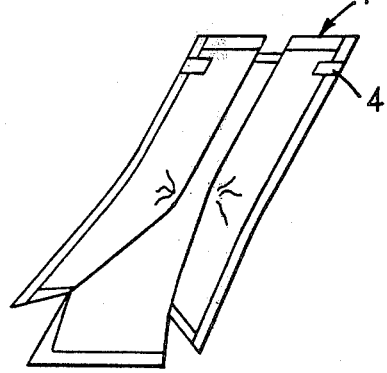
FIGS. 1 through 3 are perspective views showing embodiments of disposable diapers.
Figure 2:
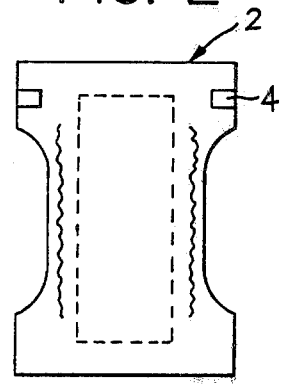
Figure 3:
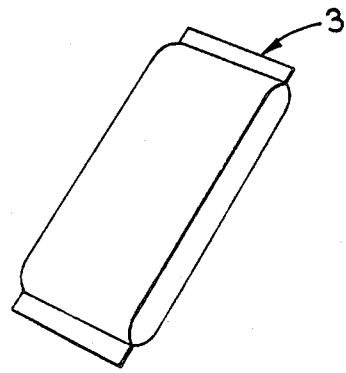

In the drawings, the reference numerals identify the following elements:

1, 2, 3: disposable diapers;
4: tape fastener
5: liquid-impermeable sheet (polyethylene sheet)
6: first absorbing layer 7: second absorbing layer (water-absorbing polymer layer)
8: porous surface sheet (non-woven fabric)
9: tissue paper (moisture-proof paper)
10: fluffed pulp (fluffed cellulosic pulp)
11: rayon staple FIGS. 1 to 3 show three conventional disposable diapers 1, 2 and 3, respectively, which can contain the absorbent article according to the invention. In FIGS 1 and 2, the diapers are provided with tape fasteners 4 for securing the diaper on the wearer. FIG. 3 shows a disposable diaper 3 similar in construction to a sanitary napkin. This construction can be used as a sanitary napkin if appropriately changed in size.

Figure 8:
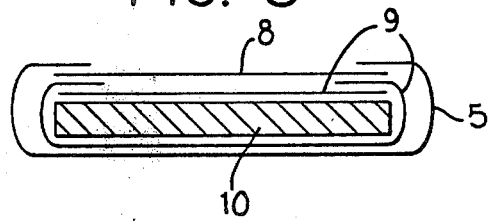
FIGS. 8 and 9 are sectional views showing conventional disposable diapers.

In FIG. 8, the diaper contains a fluffed pulp layer 10 disposed within an envelope of tissue paper 9. A liquid-impermeable sheet 5 covers the sides and bottom of the envelope and a porous surface sheet 8 covers the upper surface of the envelope.

Figure 9:
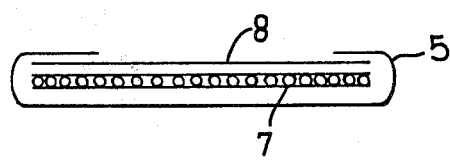

In FIG. 9, the sides and bottom of a layer 7 of super water-absorbing polymer are covered by a liquid-impermeable sheet 5 and a porous surface sheet 8 covers the upper surface of said layer.

Figure 10:
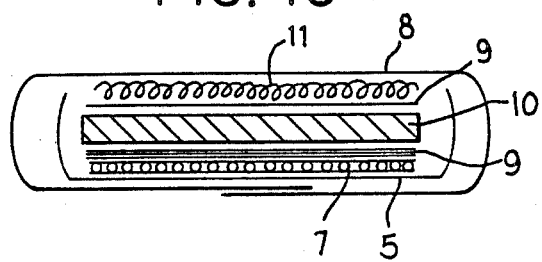
FIG. 10 is a sectional view showing an example of a commercially available sanitary napkin.

In FIG. 10, a fluffed pulp layer 10 has a tissue paper 9 and a rayon staple layer 11 on its upper surface. A plurality of tissue papers 9 and a second absorbing layer 7 are below the lower surface of the fluffed pulp layer 10. A liquid-impermeable sheet 5 covers the sides and bottom of the assembly of the elements 7, 8, 9 and 10. A porous surface sheet 8 encloses the assembly.

As shown in FIGS. 4 through 7, the absorbent article according to the present invention comprises a first absorbing layer 6 and a second absorbing layer 7. The first absorbing layer 6 is ordinarily formed of a felt obtained by bonding fibrous webs. A plastic sponge having communicating pores can also be used. A felt formed of bonded fibrous webs can easily be prepared according to a known method, but it is important to use bonded fibrous webs having a certain thickness under a load of 35 g/cm$^2$ in the wet state, that is, the webs exhibit a certain springiness or repelling force so that they do not compress excessively. More specifically, it is critical that the basis weight (the weight per m$^2$) of the first absorbing layer 6 should be 15 to 50 g and its density under a load of 35 g/cm$^2$ in the wet state should be lower than 0.045 g/cm$^3$, preferably lower than 0.03 g/cm$^3$, not including the density of the absorbed fluid. When this first absorbing layer 6 is combined with the super water-absorbing polymer, it is preferred that the first layer 6 should have an area sufficient to cover the entire surface of the second absorbing layer 7. The bonded fibrous webs of the first absorbing layer 6 can be made of large denier fibers because such fibers show a repelling force. Either synthetic fibers or semi-synthetic fibers can be used. However, if large denier fibers are used, there occurs the undesirable phenomenon that the first absorbing layer 6 becomes stiff as a whole. As a means for eliminating this disadvantage, a conventional porous surface sheet 8, for example, a non-woven fabric (having a basis weight of 15 to 20 g/m$^3$) can be disposed on top of the upper absorbing layer 6. As fibers having a repelling force and a soft feel, 30 to 60 wt. % of hollow polyester fibers having, for example, a fineness of 6 to 12 deniers, can be mixed in the first absorbing layer 6. In order to attain the objects of the present invention, synthetic fibers having a modified cross section, e.g. non-circular, for example, polyester, nylon and acrylic fibers, are used for producing a repelling force, and moreover, highly crimped fibers having a fineness of 3 to 6 deniers and hollow cross section fibers having a fineness of 6 to 12 deniers can also be used. As other fibers to be mixed in the surface sheet 8, fine fibers having a fineness of 1 to 3 deniers are used mainly for producing a good touch and feel. In order to reduce the wet back amount, there can be used synthetic fibers having no water-absorbing property, such as polyester and nylon fibers, but when the prevention of leakage is important, hydrophilic fibers such as rayon fibers, can be used. As the other critical component, there can be mentioned a binder. An emulsion resin customarily used as the binder for a non-woven fabric can be used. ES fibers supplied by Chisso Kabushiki Kaisha, which are heat-fusible composite fibers, are preferably used as the binder. ES fibers having a fineness of about 3 deniers are especially preferred. When strength is important, the ES fibers are preferably mixed at a ratio of about 50% by weight. Ordinarily, the mixing ratio of ES fibers is 30 to 50% by weight.

The leakage referred to herein includes two kinds. More specifically, one is a leakage which is caused because there is an insufficient absorbing property, and the other leakage is a leakage which is caused because liquid flows on the surface because the rate of absorption is too slow. In the present invention, it is intended to prevent the former leakage. The latter leakage can be prevented by a known method for adjusting the surface energy of fibers by treating the fiber surfaces with a surface active agent composition. The former leakage cannot be prevented by any of the known methods.

The second absorbing layer 7 as one of the structural elements of the present invention will now be described. A super water-absorbing polymer is fixed to be second absorbing layer 7. Ordinarily, the super water-absorbing polymer is scattered between two water-absorbing papers and the polymer is bonded and fixed to those papers by water or heat. Furthermore, there can be adopted a method in which a fluff pulp is mixed with a super water-absorbing polymer and the mixture is compression-molded to form a sheet. Moreover, the second absorbing layer 7 can easily be prepared according to various known methods. The super water-absorbing polymer that is used in the present invention is a polymer that can absorb water in an amount of at least 10 times its own weight. For example, there can be used carboxylated cellulose, hydrolyzed acrylonitrile-grafted starch, acrylic acid derivative polymers, polyacrylonitrile derivatives, polyacrylamide type compounds and saponified vinyl acetate/methyl acrylate copolymers. Among these polymers, acrylic acid derivative copolymers are especially preferred. These polymers are marketed under trademarks "Sanwet" (supplied by Sanyo Kasei Kogyo Kabushiki Kaisha) and "Sumika Gel" (supplied by Sumitomo Kagaku Kabushiki Kaisha). The amount of the super water-absorbing polymer is determined according to the absorbing capacity of the polymer. For example, when the urine absorbing capacity is 40 to 50 g/g, in the case of a standard size diaper, the polymer is used in an amount of 3 to 4 g/sheet. In this case, when a conventional fluff pulp is used, it must be used in an amount of 35 to 40 g/sheet. Ordinarily, the super water-absorbing polymer powder is uniformly and randomly scattered on the fluff pulp at a rate of 20 to 100 g/m$^2$, but the polymer may be arranged in patterns, such as lines. The amount scattered of the polymer powder is made different according to whether or not the second absorbing layer 7 having the super water-absorbing polymer fixed thereto covers the entirety or only part of the surface of the diaper. It is preferred that the super water-absorbing polymer be provided only in an area where a high absorbing efficiency is required. As the wetting property of the super water-absorbing polymer surface is higher, the amount scattered can be increased. The above-mentioned "Sumika Gel" can be provided in a larger amount than "Sanwet". In the case of a standard size absorbent article, the sum of the weight of the absorbent in both the first and second absorbing layers is 12 to 14 g/sheet in the present invention, which is much smaller than the weight of the conventional fluff pulp, which is 35 to 40 g/sheet. Accordingly, the weight of the absorbent article can be reduced according to the present invention.

As shown in FIGS. 4 through 7, the absorbent article of the present invention comprises, in addition to the above-mentioned first and second absorbing layer 6 and 7, a liquid-impermeable sheet 5, a water-absorbing paper or moisture-proof water-absorbing paper 9 and a porous surface sheet 8. A low-density polyethylene sheet is ordinarily used as the liquid-impermeable sheet, and in case of a sanitary napkin, a laminate comprising a non-woven fabric and a thermoplastic resin is ordinarily used. Commercially available products can be used as the water-absorbing or moisture-proof water-absorbing paper 9 and porous surface sheet 8.

The present invention will now be described in detail with reference to the following Examples and Production Examples directed to diapers. In these Examples, all references to "%" are percent by weight unless otherwise indicated.

PRODUCTION EXAMPLE 1

50% of polyester hollow fibers having a fineness of 12 deniers and a fiber length of 56 mm, which were manufactured and supplied by Teijin Limited, were mixed with 50% of ES fibers having a fineness of 3 deniers and a fiber length of 51 mm, which were manufactured and supplied by Chisso Kabushiki Kaisha, and the mixed fibers were passed through an ordinary roller carding machine to obtain webs having a basis weight of 15, 25 or 50 g/m². These webs were bonded at intervals of 4 mm according to a known method to form a first absorbing layer 6.

PRODUCTION EXAMPLE 2

45% of polyester hollow fibers having a fineness of 12 deniers and a fiber length of 56 mm, which were manufactured and supplied by Teijin Limited, were mixed with 45% of ES fibers having a fineness of 3 deniers and a fiber length of 51 mm, which were manufactured and supplied by Chisso Kabushiki Kaisha, and 10% of polynodic rayon fibers having a fineness of 3 deniers and a fiber length of 65 mm, which were manufactured and supplied by Daiwabo Kabushiki Kaisha, and the mixed fibers were passed through an ordinary roller carding machine to obtain webs having a basis weight of 25 g/m². These webs were bonded at an interval of 3 mm according to a known method to form a first absorbing layer 6.

Comparison bonded webs were prepared in the same manner by using various fibers, as follows:

PRODUCTION EXAMPLE 3

35% of polyester hollow fibers having a fineness of 12 deniers and a fiber length of 56 mm;

40% of ES fibers having a fineness of 3 deniers and a fiber length of 51 mm;
25% of polynodic rayon fibers having a fineness of 3 deniers and a fiber length of 65 mm;
Basis weight of 25 g/m².

PRODUCTION EXAMPLE 4

50% of polyester fibers having a fineness of 3 deniers and a fiber length of 56 mm;
50% of ES fibers having a fineness of 3 deniers and a fibers length of 51 mm;
Basis weight of 25 g/m².

The physical properties of the webs prepared in the foregoing Production Examples are shown in Table 1.

TABLE 1

| Sample No. | Basis Weight (g/m²) | Density (g/cm³) under Compression of 35 g/cm² | |
|---|---|---|---|
| | | Dry State | Wet State** |
| Production Example 1 (Invention) | 1 | 50 | 0.026 | 0.025 |
| Production Example 1 (Invention) | 2 | 25 | 0.025 | 0.026 |
| Production Example 1 (Invention) | 3 | 15 | 0.029 | 0.037 |
| Production Example 2 (Invention) | 4 | 25 | 0.026 | 0.038 |
| Production Example 3 (Comparison) | 5 | 25 | 0.029 | 0.051 |
| Production Example 4 (Comparison) | 6 | 25 | 0.053 | 0.078 |
| Angel Star Pure Safety Web* (Comparison) | 7 | 43 | 0.043 | 0.086 |

Note
*safety web in the product Angel Star Pure (napkin manufactured by Angel Kabushiki Kaisha)
**density of wet web excluding the density of water The above webs were formed into absorbent articles by using the materials described below.

(1) Webs of Samples Nos. 1 through 7 having a size of 300 mm × 400 mm.

(2) Water-absorbing polymer sheets (super water-absorbing polymer sandwiched between two tissue papers) having a size of 300 mm × 370 mm and a super water-absorbing polymer (Sumika Gel supplied by Sumitomo Kagaku Kabushiki Kaisha) fixed therein in an amount of 3 g.

(3) Non-woven fabrics (surface sheets) having a basis weight of 20 g/m², which were prepared by fusion-bonding 45% of polyester fibers having a fineness of 1.4 deniers and a fiber length of 51 mm and 55% of ES fibers having a fineness of 3 deniers and a fiber length of 51 mm.

(4) Moisture-proof papers (tissue papers) having a basis weight of 20 g/m².

(5) Liquid-impermeable back sheets formed of a polyethylene film having a basis weight of 20 g/m² (manufactured bu Clopay Corp.).

EXAMPLES 1 THROUGH 4 AND COMPARATIVE EXAMPLES 1 THROUGH 3

Figure 5:
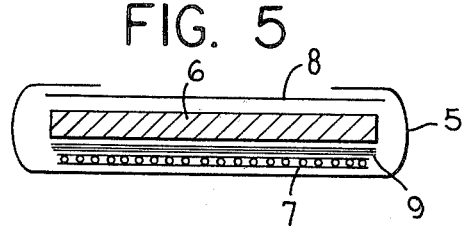
Figure 6:
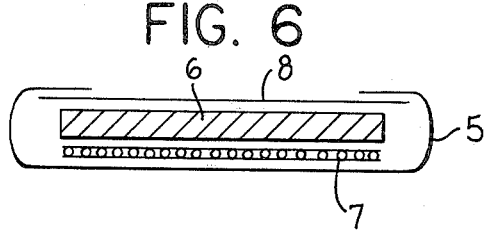
Figure 7:
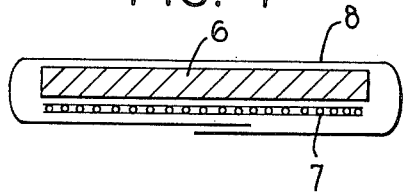

As shown in FIG. 5, a water-absorbing polymer sheet 7, three tissue papers 9, a web 6 selected from Samples 1 through 7 and a non-woven fabric were piled up in this order on a polyethylene sheet 5 to form an absorbent article.

EXAMPLE 5 AND COMPARATIVE EXAMPLE 4

Figure 4:
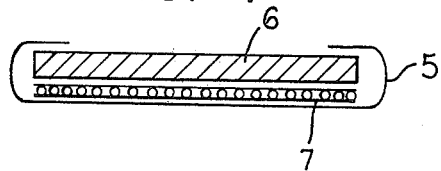
FIGS. 4 through 7 are sectional views showing embodiments of the absorbent article according to the present invention.

As shown in FIG. 4, a water-absorbing polymer sheet 7 and a web 6 of Sample No. 4 or 5 were piled up in this order on a polyethylene sheet 5 to form an absorbent article.

EXAMPLE 6

An absorbent article as shown in FIG. 5 was prepared by using a web of Sample No. 2 and a sheet 7 obtained by mixing a fluff pulp and a super water-absorbing polymer at a ratio shown below and molding the mixture into a sheet.
Fluff pulp: 6 g of SAM supplied by Weyerhaeuser Co. Super water-absorbing polymer: 2 g of Sumika Gel.

COMPARATIVE EXAMPLE 5

As shown in FIG. 8, a tissue of paper 9, a fluffed pulp 10 (36 g of SAM supplied by Weyerhaeuser Co.), a tissue paper 9 and a non-woven fabric 8 were piled up in this order on a polyethylene sheet 5 to obtain a commercially available throwaway diaper.

Data of the absorbing speed and wet back amount of the thus-obtained absorbent articles are shown in Table 2.

TABLE 2

| | Web No. | Absorption Time (seconds) | Wet Back Amount (g) |
|---|---|---|---|
| Example 1 | 1 | 38 | 0.26 |
| Example 2 | 2 | 46 | 0.44 |
| Example 3 | 3 | 55 | 1.76 |
| Example 4 | 4 | 62 | 2.03 |
| Comparative Example 1 | 5 | 141 | 4.01 |
| Comparative Example 2 | 6 | 232 | 5.87 |
| Comparative Example 3 | 7 | 320 | 7.23 |
| Example 5 | 4 | 33 | 3.11 |
| Comparative Example 4 | 5 | 79 | 6.89 |
| Example 6 | 2 | 41 | 0.39 |
| Comparative Example 5 | — | 202 | 4.00 |

Absorption Time:

A hole having a diameter of 1 cm was formed on the bottom of a vessel placed on the surface of the absorbent (so that a load of 35 g/cm$^2$ was applied around the hole), and the time required for absorption of artificial urine (having a surface tension adjusted to 50±3 dyn/cm) through this hole was measured.

Wet Back Amount:

After 2 minutes had passed from the time of completing absorption of the artificial urine, a load of 40 g/cm$^2$ was applied to an area of 100 cm$^2$ around the absorption point, and the liquid leaking out of the absorbent article was absorbed in a filter paper and the amount of the liquid absorbed in the filter paper was measured.

From the foregoing results, it will readily be understood that the absorbent article of the present invention has a higher capacity than conventional absorbent articles.

The embodiments of the invention in which an exclusive property or privilege is claimed are defined as follows:

1. An absorbent article, comprising: an upper, first, absorbing layer having a density, in both the dry state and the wet state, of less than 0.045 g/cm$^3$ when measured under a load of 35 g/cm$^2$, wherein the density in the wet state does not include the density of absorbed liquid, said first absorbing layer weighing from 15 to 50 g/m$^2$, said first absorbing layer being a felt made of bonded fibrous webs and being comprised of from 30 to 60% by weight of hollow polyester fibers and from 30 to 50% by weight of heat-fusible fibers; and a lower, second, absorbing layer having a super water-absorbing polymer fixed thereto.

2. An absorbent article as claimed in claim 1, wherein said hollow, polyester fibers have a fineness of from about 6 to about 12 denier and said heat-fusible fibers have a fineness of about 3 denier.

3. An absorbent article as claimed in claim 1 or claim 2 in which said super water-absorbing polymer is a powder of a polymer of an acrylic acid derivative.

4. An absorbent article as claimed in claim 1 or claim 2, in which said super water-absorbing polymer is a powder fixed between two water-absorbing sheets, said super water-absorbing polymer being capable of absorbing water in an amount at least 10 times its own weight.

5. An absorbent article as claimed in claim 1 in the form of a sheet wherein the sum of the weights of said first layer and said second layer is from about 12 to about 14 g/sheet.

6. An absorbent article as claimed in claim 1 wherein said density is lower than 0.03 g/cm$^3$.

7. An absorbent article as claimed in claim 1 wherein said first absorbing layer covers the entire surface of said second absorbing layer.

* * * * *